United States Patent
Ichihara et al.

(10) Patent No.: US 8,160,338 B2
(45) Date of Patent: Apr. 17, 2012

(54) X-RAY CT APPARATUS AND MYOCARDIAL PERFUSION IMAGE GENERATING SYSTEM

(75) Inventors: Takashi Ichihara, Nagoya (JP); Richard T. George, Sparks, MD (US); Joao A. C. Lima, Timonium, MD (US); Albert C. Lardo, Baldwin, MD (US)

(73) Assignees: Toshiba Medical Systems Corporation, Otawara-shi (JP); The Johns Hopkins University, Baltimore, MD (US)

( * ) Notice: Subject to any disclaimer, the term of this patent is extended or adjusted under 35 U.S.C. 154(b) by 918 days.

(21) Appl. No.: 12/123,776

(22) Filed: May 20, 2008

(65) Prior Publication Data

US 2009/0129536 A1    May 21, 2009

(30) Foreign Application Priority Data

Nov. 20, 2007    (JP) .................................. 2007-300551

(51) Int. Cl.
*G06K 9/00* (2006.01)
(52) U.S. Cl. .......................................... 382/131; 378/4
(58) Field of Classification Search ................ 378/4–20; 382/131; 600/425, 407, 431
See application file for complete search history.

(56) References Cited

U.S. PATENT DOCUMENTS
2005/0277830 A1    12/2005    Ichihara
2006/0241402 A1*   10/2006    Ichihara et al. ............... 600/425

FOREIGN PATENT DOCUMENTS
| EP | 1604612 A1 | 12/2005 |
| EP | 1967140 A1 | 9/2008 |
| JP | 2006-21022 | 1/2006 |
| JP | 2006-247388 | 9/2006 |

OTHER PUBLICATIONS

Kenneth A. Miles, M.D. et al., "Application of CT in the Investigation of Angiogenesis in Oncology", XP 5307854A, Academic Radiology, vol. 7, No. 10, Oct. 1, 2000, pp. 840-850.
Richard T. George, et al., "Multidetector Computer Tomography Myocardial Perfusion Imaging During Adenosine Stress", Journal of the American College of Cardiology, vol. 48, No. 1, 2006, pp. 153-160.

* cited by examiner

*Primary Examiner* — Hoon Song
(74) *Attorney, Agent, or Firm* — Oblon, Spivak, McClelland, Maier & Neustadt, L.L.P.

(57) ABSTRACT

An apparatus includes a transformation table acquiring unit, a blood-flow information acquisition unit and a blood-flow image generating unit. The transformation table acquiring unit obtains a transformation table for transforming unspecified information representing a concentration of a contrast medium in a myocardium into an unspecified blood flow value image based on a CT image acquired in a concentration transition period. The blood-flow information acquisition unit obtains information representing the concentration of the contrast medium based on a CT image acquired during a constant concentration period. The blood-flow image generating unit generates a blood flow value image based on the information representing the concentration of the contrast medium according to the transformation table.

8 Claims, 10 Drawing Sheets

X-RAY CT APPARATUS AND MYOCARDIAL PERFUSION IMAGE GENERATING SYSTEM

BACKGROUND OF THE INVENTION

1. Field of the Invention

The present invention relates to an X-ray CT (computed tomography) apparatus and a myocardial perfusion image generating system for generating myocardial perfusion image with continuously injecting a contrast medium.

2. Description of the Related Art

With a myocardial contrast examination using an X-ray CT apparatus, a contrast medium is injected into an object that is a patient, and contrast CT images are collected. Subsequently, moving images of coronary arteries, endocardial lumen wall, and so forth, are generated from the collected contrast CT images, and are employed for diagnosis.

Also, a blood flow dynamic state (perfusion) examination of the myocardium and a perfusion examination regarding organs such as within a brain tissue have been performed using an X-ray CT apparatus. With these perfusion examinations, attempting to generate a perfusion image by analyzing dynamic contrast CT data obtained from dynamic imaging by bolus injection for injecting a contrast medium in a short period has been conventionally studied.

Normally, such myocardial perfusion imaging is not an isolated examination, but performed as part of a contrast examination of a heart. For example, in the event of a myocardial perfusion image, scanning for heart function analysis such as coronary arteries and endocardial lumen movement is also performed as well as scanning of a myocardial perfusion image. Accordingly, it takes a long time for scanning of a myocardial perfusion image. An examination method resulting in increase of X-ray dosages for an object is hardly acceptable, and accordingly, long-period dynamic imaging using an X-ray CT apparatus has never come into practical use so far.

Furthermore, in order to perform all of the above-mentioned scans, it is necessary to increase the number of injection times and an injection amount of the contrast medium. However, an amount of the contrast medium which can be injected into an object has a limit. Accordingly, an imaging period is limited in view of not only dosage due to X-ray but also an injection amount of the contrast medium having a limit.

To such a problem, a technology to obtain blood flow information based on information including a coronary contrast CT image data and a myocardial contrast CT image data obtained by a scan for obtaining a myocardial image is devised without adding a scan for obtaining blood flow information to generate a myocardial perfusion image in more short time reducing a contrast medium injection volume to an object and exposure by X-ray.

This is a technology to extract the information related to a myocardial perfusion from a coronary contrast CT data and a myocardial contrast CT data by data processing for imaging since the information related to the myocardial perfusion serving as an index of a blood flow dynamic state on a myocardial region is included in the coronary contrast CT data and the myocardial contrast CT data acquired by a continuous contrast medium injection under a fixed condition. Specifically, during contrast medium is flowing with a constant concentration in a myocardial region and a coronary artery after static contrast medium injection into an object, a myocardial contrast CT image is obtained. Since a distribution image of contrast medium component obtained by subtracting the CT value of myocardium from the obtained myocardial contrast CT image has proportional relation to blood flow perfusion, the distribution image of contrast medium component is considered as a blood flow perfusion image indicating a relative blood flow perfusion (see, for example, Japanese Patent Application (Laid-Open) No. 2006-21022).

In addition, it is possible to convert a relative value of a myocardial blood flow image to an absolute value by calculating an unknown approximately using ECG synchronous CT image data acquired in a transitional period of concentration of contrast medium (see, for example, Japanese Patent Application (Laid-Open) No. 2006-247388). This allows generating a clinically-useful absolute value image (generally called a blood flow value image) of blood flow and a distribution image of local myocardial blood flow myocardium-wide.

As a related technology, the attempt to obtain a transforming function f(MBF) for transforming myocardial blood flow (MBF) to a ratio Cmyo/Ca between a concentration Ca of contrast medium in a left ventricle lumen of heart and a concentration Cmyo of contrast medium in blood of myocardium is performed (see, for example, George et al. Multidetector Computed Tomography Myocardial Perfusion Imaging During Adenosine Stress", Journal of the American College of Cardiology, Vol. 48, No. 1, 2006).

In a contrast examination of a coronary artery by an X-ray CT apparatus, measuring a stenosis ratio of a thicker blood vessel portion such as the base of coronary artery and analysis in shape and aspect of a plaque in a stenosis part is becoming possible. As a result, though an imaging period subjects to constrain for imaging a myocardial perfusion image as described above, it is desired to measure a blood flow in a myocardial portion with higher accuracy without increasing an X-ray dosage and an injection amount of the contrast medium to generate a local myocardial blood flow value image with higher accuracy.

Particularly, if a contrast examination of a coronary artery and imaging of a myocardial blood flow value image with high accuracy can be performed at the same time, estimation of a stenosis in a thinner terminal coronary artery and estimation of a stenosis in a coronary artery of an object having a remarkably calcified coronary artery of which stenosis ratio is difficult to be measured, which could not be observed by an examination using an X-ray CT apparatus conventionally, become possible. Therefore, it is desired to obtain a local myocardial blood flow value image with higher accuracy without increasing dosage and contrast medium as described above.

SUMMARY OF THE INVENTION

The present invention has been made in light of the conventional situations, and it is an object of the present invention to provide an X-ray CT apparatus and a myocardial perfusion image generating system which can acquire a myocardial perfusion image accurately in a shorter period without increasing the amount of injection of a contrast medium as to an object and dosage due to X-ray.

The present invention provides an X-ray CT apparatus for exposing X-ray to a object to scan the object and reconstructing a CT image in the object based on obtained projection data, comprising: a transformation table acquiring unit configured to obtain a transformation table for transforming unspecified information representing a concentration of a contrast medium in a myocardium into an unspecified blood flow value image of the myocardium based on a CT image acquired in a concentration transition period defined to be a period from immediately after starting of a continuously injection of the contrast medium into the object until the contrast medium injected reaches to the myocardium, increases, and is to be in a state where it can be considered that the contrast medium is saturated in a constant value; a blood-flow information acquisition unit configured to obtain information representing the concentration of the contrast medium in the myocardium of the object based on a CT image acquired during a constant concentration period during which the concentration of the contrast medium in the myocardium can be considered to be constant; and a blood-flow image generating unit configured to generate a blood flow value image based on the information representing the concentration of the contrast medium in the myocardium in the myocardium according to the transformation table, in an aspect to achieve the object.

The present invention also provides an X-ray CT apparatus comprising: a contrast-medium injector configured to obtain a concentration transition period defined to be a period from immediately after starting of a continuously injection of a contrast medium into a object until injected the contrast medium reaches to a myocardium, increases, and is to be in a state where it can be considered that the contrast medium is saturated in a constant value and a constant concentration period in which a concentration of the contrast medium in the myocardium can be considered to be constant following the concentration transition period; an image acquiring unit configured to acquire a CT image during the concentration transition period and a CT image during the constant concentration period each synchronized with an electrocardiogram; a transformation table acquiring unit configured to obtain a transformation table for transforming unspecified information representing the concentration of the contrast medium in the myocardium into an unspecified blood flow value image of the myocardium based on the CT image acquired in the concentration transition period; a blood-flow information acquisition unit configured to obtain information representing the concentration of the contrast medium in the myocardium of the object based on the CT image acquired during the constant concentration period; and a blood-flow image generating unit configured to generate a blood flow value image based on the information representing the concentration of the contrast medium in the myocardium in the myocardium according to the transformation table, in an aspect to achieve the object.

The present invention also provides a myocardial perfusion image generating apparatus comprising: a transformation table acquiring unit configured to obtain a transformation table for transforming unspecified information representing a concentration of a contrast medium in a myocardium into an unspecified blood flow value image of the myocardium based on a CT image acquired in a concentration transition period defined to be a period from immediately after starting of a continuously injection of the contrast medium into the object until the contrast medium injected reaches to the myocardium, increases, and is to be in a state where it can be considered that the contrast medium is saturated in a constant value; a blood-flow information acquisition unit configured to obtain information representing the concentration of the contrast medium in the myocardium of the object based on a CT image acquired during a constant concentration period during which the concentration of the contrast medium in the myocardium can be considered to be constant; and a blood-flow image generating unit configured to generate a blood flow value image based on the information representing the concentration of the contrast medium in the myocardium in the myocardium according to the transformation table, in an aspect to achieve the object.

The X-ray CT apparatus and the myocardial perfusion image generating system as described above make it possible to acquire a myocardial perfusion image accurately in a shorter period without increasing the amount of injection of a contrast medium as to an object and dosage due to X-ray.

DESCRIPTION OF THE PREFERRED EMBODIMENTS

An X-ray CT apparatus and a myocardial perfusion imaging generating system according to the present invention will now be described in further detail below with reference to embodiments in conjunction with the accompanying drawings.

Figure 1:
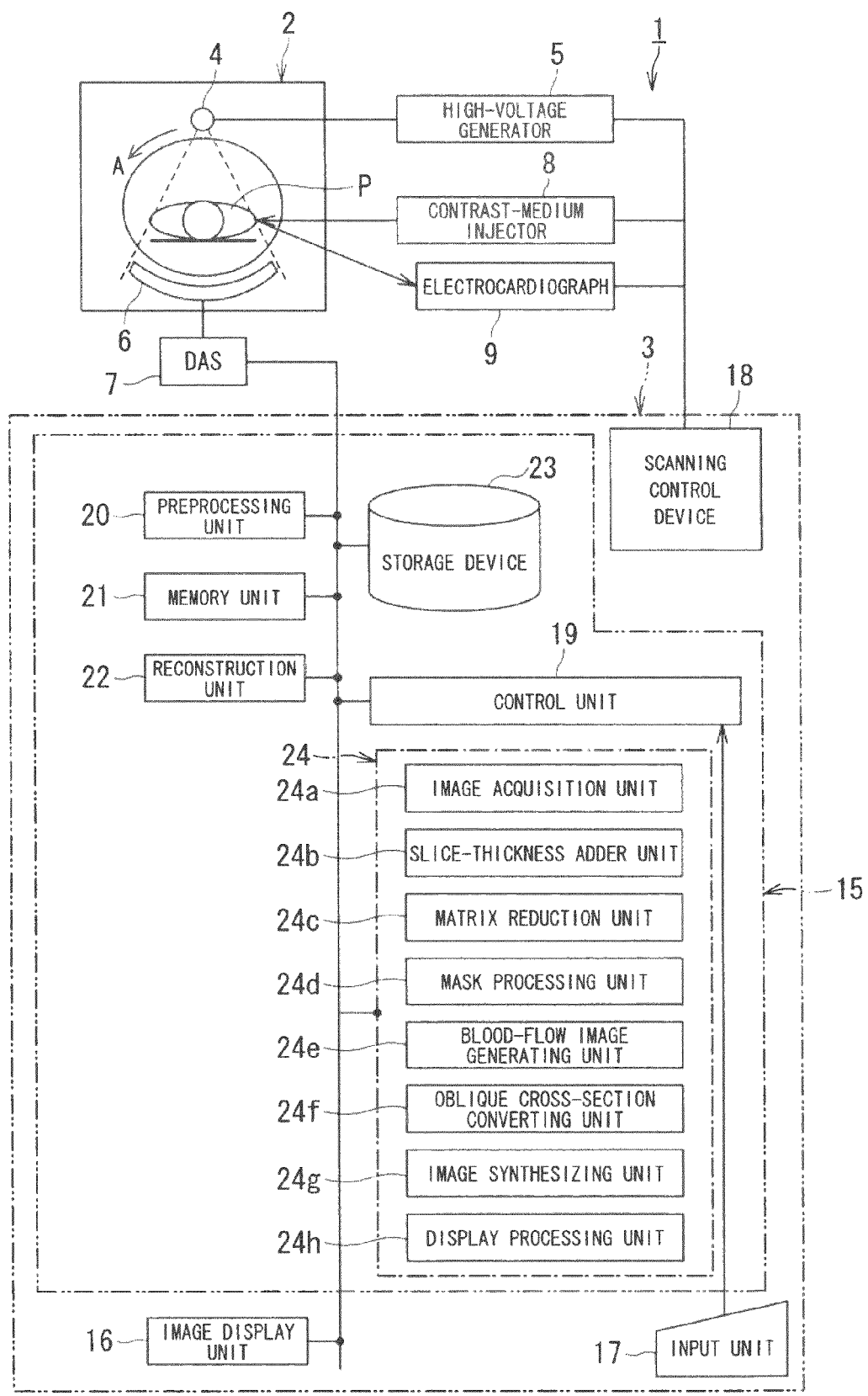
FIG. 1 is a configuration diagram illustrating an X-ray CT apparatus according to an embodiment of the present invention.

FIG. 1 is a configuration diagram illustrating an X-ray CT apparatus according to an embodiment of the present invention.

An X-ray CT apparatus 1 includes a gantry unit 2 and a computer device 3. The gantry unit 2 includes an X-ray tube 4, a high-voltage generator 5, an X-ray detector 6, a DAS (Data Acquisition System) 7, a contrast-medium injector 8, and an electrocardiograph 9. The X-ray tube 4 and the X-ray detector 6 are mounted at positions facing each other sandwiching an object P in an unshown rotating ring consecutively rotating at a high speed.

The contrast-medium injector 8, which is controlled by a control signal from the computer device 3, has a function for continuously injecting a contrast medium into the object P in accordance according to certain conditions. The contrast-medium injector 8 can control the amount and concentration of the contrast medium to be injected into the object P based on the behavior of the contrast medium within the object P.

Figure 2:
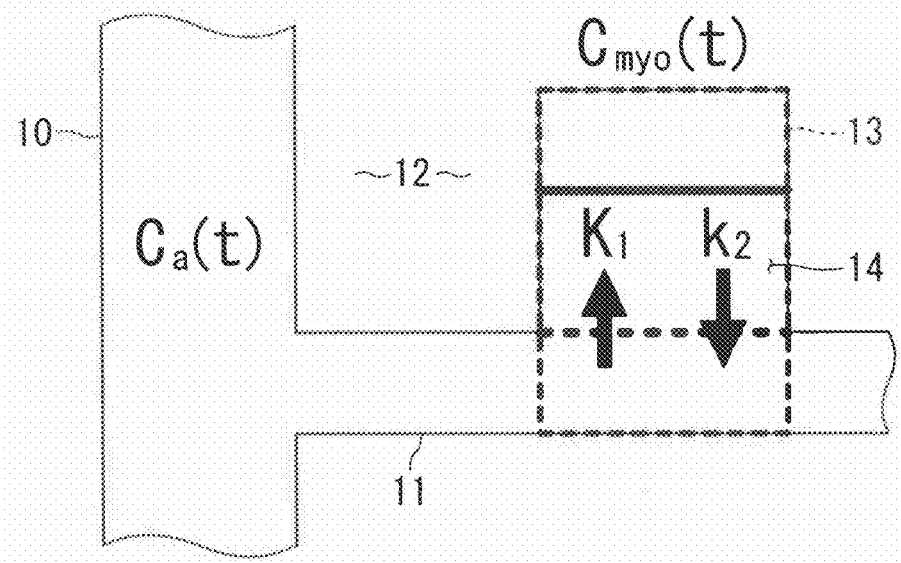
FIG. 2 is a diagram illustrating a model of the behavior of a contrast medium in the heart, within the myocardium, and within a coronary artery of an object.

FIG. 2 is a diagram illustrating a model of the behavior of a contrast medium in the heart, within the myocardium, and within a coronary artery of an object.

The unshown aorta branches off to a coronary artery 10, and the coronary artery 10 further branches off to a capillary 11, within the object P. The capillary 11 is introduced into the myocardium 12, and the myocardium 12 comprises the capillary 11 and a myocardial cell 13. The myocardial cell 13 includes a region referred to as a framework 14, and is configured such that the blood can move in and out between the framework 14 and the capillary 11.

Consequently, when a contrast medium is injected into the object P, the contrast medium is led from the aorta to the coronary artery 10 along with the blood, and led from the coronary artery 10 to the capillary 11. Furthermore, when the contrast medium flows along with the blood within the capillary 11, and reaches the myocardial cell 13, part of the contrast medium flows in the framework 14 within the myocardial cell 13 from the capillary 11. Moreover, the part of the blood flowed in the framework 14 within the myocardial cell 13 flows out of the myocardial cell 13 and moves in the capillary 11 again.

Accordingly, the concentration of the contrast medium in blood within the aorta or coronary artery 10 and the concentration of the contrast medium in blood within the myocardial cell 13 or capillary 11 exhibit different values, and change over time due to movement of the contrast medium. The concentration of the contrast medium in blood within each portion of the object P is determined by a transitional constant at the time of the contrast medium flowing in the framework 14 within the myocardial cell 13 from the capillary 11, and a transitional constant at the time of the contrast medium flowing in the capillary 11 from the framework 14 within the myocardial cell 13.

More specifically, let us say that the concentration of the contrast medium within the left ventricular lumen (blood pool in left ventricle) or the coronary artery in time t is Ca(t), a region included in the myocardium 12, which includes the capillary 11 and myocardial cell 13, is a unit region, the concentration of the contrast medium within the blood in the myocardium 12 (the average concentration of the contrast medium within the capillary 11 and myocardial cell 13) is Cmyo(t), a transitional constant at the time of the contrast medium flowing in the framework 14 within the myocardial cell 13 from the capillary 11 is K1, and a transitional constant at the time of the contrast medium flowing out of the capillary 11 to the framework 14 within the myocardial cell 13 is k2, Ca(t) and Cmyo(t) are determined by the transitional constant K1 and the transitional constant k2.

Figure 3:
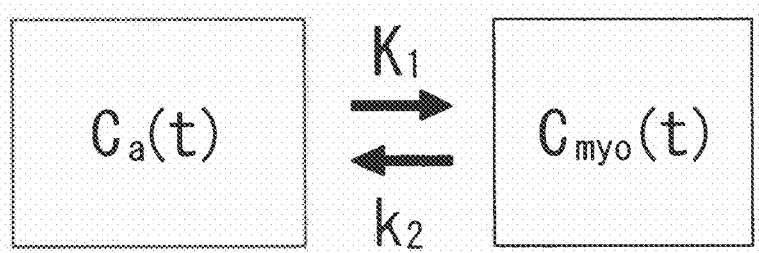
FIG. 3 is a diagram conceptually representing the model illustrated in FIG. 2 using parameters.

FIG. 3 is a diagram conceptually representing the model illustrated in FIG. 2 using parameters.

As illustrated in FIG. 3, while the contrast medium having the concentration Ca(t) and the amount proportional to the transitional constant K1 moves in the framework 14 of the myocardial cell 13 from the capillary 11, the contrast medium having the concentration Cmyo(t) and the amount proportional to the transitional constant k2 moves in the capillary 11 from the framework 14 of the myocardial cell 13 at certain time t. Subsequently, the concentration Ca(t) and concentration Cmyo(t) of the contrast medium following movement are determined the transitional constant K1 and transitional constant k2.

Accordingly, the concentration Cmyo(t) of the contrast medium within the myocardium 12 at a certain time t can be represented by the difference between the amount of the contrast medium flowing in the framework 14 and the amount of the contrast medium flowing out of the framework 14, thereby satisfying the following Expression (1).

$$dCmyo(t)/dt = K1 \cdot Ca(t) - k2 \cdot Cmyo(t) \quad (1)$$

By resolving the Expression (1) analytically, the Expressions (2-1), (2-2), (2-3) and (2-4) are derived. Specifically, a concentration Cmyo(t) the contrast medium in the myocardium 12 at time t can be represented by using the transitional constant K1 and the transitional constant k2.

$$Cmyo(t) = K1 \int_0^t Ca(\tau) \exp\{-K1(t-\tau)/Vd\} d\tau \quad (2\text{-}1)$$

$$Vd = K1/k2 \quad (2\text{-}2)$$

wherein $$K1 = E \cdot MBF \quad (2\text{-}3)$$

$$E = 1 - \exp(-PS/MBF) \quad (2\text{-}4)$$

In the Expressions (2-1) and (2-4), E denotes a value (Extraction efficiency) representing a ratio of the contrast medium in blood flow concentration, PS denotes a Permeability-Surface area Product, MBF denotes a myocardial blood flow [ml/100 g/min] per a unit time and per a unit weight serving as an index of myocardial blood perfusion. The Expression (2-3) presents relationship between the transitional constant K1 and the myocardial blood flow (MBF). Further, the Extraction efficiency E is a function of the myocardial blood flow (MBF) as indicated by the Expression (2-4). An accurate value of Extraction efficiency E or the relational Expression (2-4) for calculating the Extraction efficiency E can be calculated in advance by comparing a PET (positron emission computed tomography) examination with a CT examination or a known method. Since it is known that Vd of the Expressions (2-1) and (2-2) shows a constant value in a normal myocardium, Vd can be determined by an examination or the like in advance.

Therefore, when the concentration Ca(t) of the contrast medium in the left ventricular lumen or a coronary artery can be obtained at injecting the contrast medium, the concentration Cmyo(t) of the contrast medium in the myocardium 12 can be calculated by the Expression (2-1). Hereinafter, a description is given in case of Ca(t) representing a TDC (time density curve) of the contrast medium concentration in the left ventricular lumen. Therefore, when a time variation curve Ca(t) of the contrast medium concentration in the left ventricular lumen can be obtained, a time variation curve Cmyo(t) of the contrast medium concentration in the myocardial portion can be calculated by the Expression (2-1).

On the other hand, heretofore, it has been known that when a contrast medium is injected statically into the object P in accordance with a certain condition, a state in which the concentrations of the contrast medium in blood within a coronary artery and the myocardium 12 are considered to be constant respectively emerges, i.e., a constant concentration period emerges.

Figure 4:
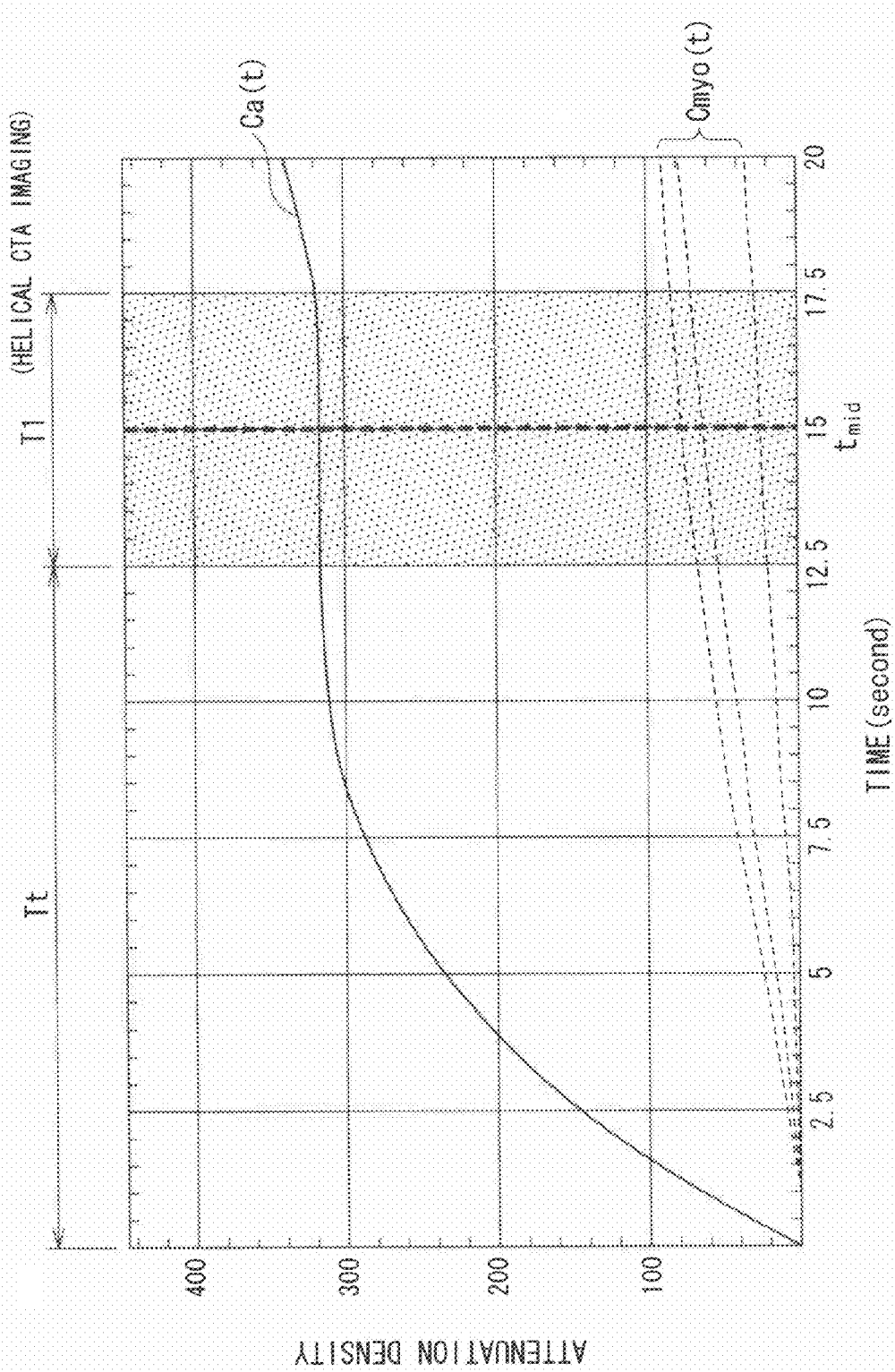
FIG. 4 is a diagram illustrating the temporal concentration variation of a contrast medium in a coronary artery or a left ventricular lumen and a myocardial portion due to continuous static injection of the contrast medium into an object using the contrast-medium injector illustrated in FIG. 1.

FIG. 4 is a diagram illustrating the temporal concentration variation of a contrast medium in a coronary artery or a left ventricular lumen and a myocardial portion due to continuous static injection of the contrast medium into an object using the contrast-medium injector 8 illustrated in FIG. 1.

In FIG. 4, the vertical axis represents a concentration C of the contrast medium, and the horizontal axis represents time t. Note that, a concentration of the contrast medium corresponds to a CT value, and therefore the vertical axis represents a CT value corresponding to a concentration of the contrast medium. Further, the solid line of FIG. 4 is data (a contrast medium concentration variation curve) indicating change-of-time of the concentration Ca(t) of the contrast medium within a coronary artery or in a left ventricular lumen and a myocardial portion and the dotted lines are data (contrast medium concentration variation curves) indicating change-of-time of the concentration Cmyo(t) of the contrast medium within the myocardial portion made up of the myocardial cell 13 and capillary 11.

After contrast medium is continuously injected in an object P, the injected contrast medium arrives at the myocardium, and consequently the concentration of the contrast medium increases. Then, a state in which the concentration Ca(t) of the contrast medium in the coronary artery and the left ventricular lumen and the concentration Cmyo(t) of the contrast medium in the myocardial region can be considered to arrive into constant values respectively, i.e., a constant concentration period T1 emerges.

Consequently, in the event that contrast examination of a myocardial portion is performed synchronously with an electrocardiogram in a constant concentration period T1 in which the concentration Cmyo(t) of the contrast medium within the myocardial region is considered to be constant, a contrast CT image can be acquired from X-ray CT data of coronary artery. Consequently, the contrast-medium injector 8 is configured so as to inject the contrast medium having a predetermined amount rate per time into the object P in accordance with a certain condition, and so as to obtain a state in which the concentration Ca(t) and concentration Cmyo(t) of the contrast medium within the coronary artery and myocardial portion are considered to be constant.

Note that the condition for injecting the contrast medium is experientially determined such that the concentration Ca(t) of the contrast medium within the coronary artery becomes constant during collection of X-ray CT data, so some difference exists in injection speed. The recommended conditions such as injection speed at the time of static injection of the contrast medium are described in documents such as "Study of Optimal Contrast Examination Method in Herical Scanning CT", by Atsusi Yamachi and Tadashi Wako, Japan-Germany Medical Reports Vol. 40 No. 2, 1995, for example.

Now, when a period immediately after injection start of the contrast medium till the constant concentration period is defined as a concentration transition period Tt, a contrast examination of the coronary artery is performed during the constant concentration period T1 which is after the concentration transition period Tt, and therefore, an contrast CT image of the coronary artery can be acquired by the contrast examination.

When the X-ray CT apparatus 1 has 64 rows of detecting elements for example, the effective field of view does not cover the entire myocardium in the body axis direction (z direction) Accordingly, a contrast CT image of the myocardial portion can be acquired by a helical CT angio-scan with moving an object so that the field of view moves to a heart apex part or a heart root part.

When a time for scan at the mid portion of the myocardium is set as a representative time $t_{mid}$ for simplifying calculation though a helical scan for acquiring a contrast CT image actually performed continuously, the concentration Cmyo($t_{mid}$) of the contrast medium in a myocardial region at the scan time $t_{mid}$ can be calculated based on the Expression (2-1). Accordingly, a function, which is described later in detail, for calculating the concentration Cmyo($t_{mid}$) of the contrast medium in a myocardial region at the scan time $t_{mid}$ is provided with the computer device 3.

On the other hand, the electrocardiograph 9 is connected to unshown electrodes connected to the object P. The electrocardiograph 9 has a function to detect an electrocardiogram signal (ECG signal) via the electrodes from the object P, generate an electrocardiogram of the object P from the detected ECG signal, and provides this to the computer device 3.

The high-voltage generator 5 is configured so as to supply a tube current or tube voltage to the X-ray tube 4 synchronously with the electrocardiogram in accordance with a control signal from the computer device 3, and so as to detect X-rays transmitting the object P using the X-ray detector 6, while the concentration Cmyo(t) and Ca(t) of the contrast medium within the coronary artery and the myocardial portion are constant or have linear properties. Furthermore, the X-ray detection signal detected by the X-ray detector 6 is provided to the DAS 7 so as to be digitized, and provided to the computer device 3.

Further, in order to know the timing at which the contrast medium passes through the portions such as the left ventricular lumen and so forth and reaches the myocardium, the X-ray CT apparatus 1 includes a function for performing dynamic acquisition of X-ray data in a concentration transition period Tt. The X-ray data dynamically acquired in this concentration transition period Tt is also given to the computer device 3 via the DAS 7. The X-ray data in a concentration transition period Tt is also used for generation of a blood flow value image by the computer device 3 as described later.

Note that a technique example for finding the timing at which the contrast medium reaches the myocardium, and the concentration transition period Tt is changed to the constant concentration period T1, is disclosed in Japanese Unexamined Patent Application Publication No. 2003-245275.

More specifically, a technique is disclosed for automatically setting the timing at which the contrast medium reaches the myocardium using an optional method such as a method for determining whether or not the contrast medium concentration (or a CT value) reaches a predetermined threshold value, a method for converting the contrast medium concentration (or a CT value) into a graph, and determining whether or not the tangential gradient angle of the graph reaches a predetermined angle, a method for converting the contrast medium concentration (or a CT value) into a graph, and determining whether or not the graph reaches a peak, or the like. However, even without employing this technique, an arrangement may be made wherein an electrocardiogram-synchronous CT image or a variation curve of the contrast medium concentration as illustrated in FIG. 4 is graphically displayed, and accordingly, the user can visually recognize the timing at which the contrast medium reaches the myocardium.

The computer device 3 includes an image processing device 15, an image display unit 16, an input unit 17, and a scanning control device 18. The scanning control device 18 has a function for providing a control signal to the high-voltage generator 5 and contrast-medium injector 8 to control these devices based on the electrocardiograms collected by the electrocardiograph 9, thereby executing collection of electrocardiogram-synchronous CT images.

In particular, the scanning control device 18 includes a function for detecting the timing at which the concentration transition period Tt is changed to the constant concentration period T1 using an arbitrary method. An arrangement is made wherein a helical scan for generating an electrocardiogram-synchronous CT image can be performed by acquiring data from the entire myocardium during the constant concentration period T1 with moving the unshown table after acquiring X-ray data during the concentration transition period Tt using the scanning control device 18.

Moreover, the image processing device 15 comprises a control unit 19 serving as a core, a preprocessing unit 20 for converting raw data to be output from the DAS 7 into projection data via correction processing and the like, a memory unit 21 for storing the projection data, an image reconstruction unit 22 for reconstructing CT image data from the projection data, a storage device 23 for storing the CT image data, and a myocardial perfusion image generating system 24 for reading the CT image data from the storage device 23 so as to generate a myocardial perfusion image.

The myocardial perfusion image generating system 24 includes an image acquisition unit 24a, a slice-thickness adder unit 24b, a matrix reduction unit 24c, a mask processing unit 24d, a blood-flow image generating unit 24e, an oblique cross-section converting unit 24f, an image synthesizing unit 24g, and a display processing unit 24h.

The image acquisition unit 24a includes a function for reading and acquiring myocardial contrast CT image data due to the contrast medium acquired during the concentration transition period Tt or myocardial CT data acquired during the concentration transition period Tt from the storage device 23, and a function for giving the acquired contrast CT image data or CT data to another element of the myocardial perfusion image generating system 24.

The slice-thickness adder unit 24b has a function for receiving myocardial contrast CT image data from the image acquisition unit 24a, and adding the contrast CT values between the adjacent slices or averaging the values, thereby reducing the resolution of the contrast CT image data in the slice direction.

The matrix reduction unit 24c has a function for receiving myocardial contrast CT image data from the image acquisition unit 24a, and subjecting the contrast CT values to adding and averaging, thereby reducing the matrix of the myocardial contrast CT image data.

The mask processing unit 24d has a function for receiving myocardial contrast CT image data from the image acquisition unit 24a, and subjecting the received CT image data to mask processing, thereby extracting a region where the blood flow of the myocardial portion exists. That is, the mask processing unit 24d functions as a region determining unit configured to determine a myocardial region.

The blood-flow image generating unit 24e has a function for generating a blood flow value image of the blood flow region or the myocardial portion extracted by the mask processing unit 24d as a myocardial perfusion image. Now, a method for generating a blood flow value image will be described.

By obtaining the variation curve Ca(t) of the contrast medium concentration in the coronary artery or the left ventricular lumen during the concentration transition period Tt after injecting the contrast medium, the concentration Cmyo (t), which corresponds to various transitional constant K1 or myocardial blood flow (MBF), of the contrast medium in the myocardial region can be calculated based on the Expression (2-1). In other words, a transformation table between the myocardial blood flow (MBF) and the concentration Cmyo(t) of the contrast medium in the myocardial region or a transformation table between the myocardial blood flow (MBF) and the ratio Cmyo(t)/Ca(t) of the concentration Cmyo(t) of the contrast medium in the myocardial region to the variation curve Ca(t) of the contrast medium concentration in the coronary artery or the left ventricular lumen can be calculated.

Further, the myocardial blood flow (MBF) can be calculated at an arbitrary time t or acquisition time of a contrast CT image of the coronary artery, i.e, at a scan time $t_{mid}$, by using a transformation table to be displayed as a blood flow value image.

Specifically, by acquiring the variation curve Ca(t) of the contrast medium concentration in the coronary artery or the left ventricular lumen during the concentration transition period Tt of the contrast medium, the myocardial blood flow (MBF) can be calculated to generate a blood flow value image. Consequently, a blood flow value image is also generated and displayed by a single scan necessary for acquiring a contrast CT image.

As mentioned above, by using existence of the concentration transition period Tt of the contrast medium during which the concentration variation of the contrast medium is not constant in the coronary artery and the left ventricular lumen, a transformation table for calculating the myocardial blood flow (MBF) from the variation curve Ca(t) of the contrast medium concentration during the concentration transition period Tt can be acquired.

Further, the CT value of myocardial contrast CT image data to be obtained by injecting the contrast medium is equal to sum of the CT value of only the myocardium serving as a myocardial tissue component and the CT value of image of a contrast medium component. Accordingly, if the CT value of only the myocardial portion is subtracted from the myocardial contrast CT image data, the concentration Cmyo(t) of the contrast medium in the myocardial portion and a concentration variation curve Ca(t), which is necessary for calculating a transformation table, of the contrast medium in the coronary artery or the left ventricular lumen. Thus, a myocardial blood flow (MBF) can be calculated based on the concentration Cmyo(t) of the contrast medium in the myocardial portion.

Consequently, the blood-flow image generating unit 24e includes a function for calculating the above-mentioned transformation table based on the myocardial CT data during the concentration transition period Tt acquired from the image acquisition unit 24a and a function for obtaining a myocardial blood flow (MBF) by subtracting the CT value of only the myocardium from the myocardial contrast CT image data in the blood flow region extracted by the mask processing unit 24d and using the transformation table to generate blood flow value image data of the myocardial portion.

That is, the blood-flow image generating unit 24e also functions as a blood-flow information acquisition unit for obtaining a concentration variation curve Ca(t) of the contrast medium by subtracting the CT value of only the myocardium from the myocardial CT data, which is received from the image acquisition unit 24a, of the coronary artery or the left ventricular lumen acquired during the concentration transition period Tt.

The oblique cross-section converting unit 24f has a function for converting the cross-section of a myocardial blood flow image generated by the blood-flow image generating unit 24e to generate a cross-sectional image at an arbitrary cross-section, e.g., a circular cross-sectional image with the longitudinal direction of the myocardium serving as an axis thereof.

The image synthesizing unit 24g has a function for synthesizing an image having a high resolution prior to the matrix reduction processing and adding the contrast CT value between slices, i.e., the image data of the mask region of the myocardial contrast CT image data received from the image acquisition unit 24a with the myocardial blood flow image generated by the blood-flow image generating unit 24e so as to generate a synthesized image, and superimposing both of the image and the data at the same position on a screen, each of which an arbitrary value such as transparency is adjusted so as to display both of the image and the data.

The display processing unit 24h has a function for providing to the image display unit 16 image signals for displaying the respective images such as blood flow images, oblique cross-sectional images, and synthesized images, which are generated by the blood-flow generating unit 24e, oblique cross-section converting unit 24f, and image synthesizing unit 24g respectively, and a function for setting display conditions so as to visually recognize a blood flow image in each displayed image.

Moreover, the display processing unit 24h is configured so as to display images for instructing the settings of display conditions on the image display unit 16 at the time of setting image display conditions, and also so as to acquire instructions for image display conditions from the input unit 17.

Examples of appropriate image display conditions include a display method for selectively displaying only blood flow images by setting the CT value of the myocardium to the lower limit of pixel values to be displayed, and also setting the value obtained by adding the contrast medium concentration Cmyo(t) in the myocardial portion to the CT value of the myocardium to the upper limit of pixel values to be displayed. Another method is one by which pixel values are set in a range between the CT value of the myocardium and the value obtained by adding the contrast medium concentration Cmyo(t) in the myocardial portion to the CT value of the myocardium. According to this method, a myocardial blood flow (MBF) can be displayed with a color corresponding to each pixel value. In this case, an arrangement may be made wherein the upper limit of pixel values can be fine-adjusted due to default values by receiving instructions information from the input unit 17.

Consequently, the display processing unit 24h may include a function for setting a value of a window level at the time of performing at least either gradation conversion and color tone conversion based on a value corresponding to the myocardial portion, and a value corresponding to the myocardium, which are contrasted by the contrast medium, or may include a function for setting a value of window level at the time of performing at least either gradation conversion and color tone conversion so as to emphasize pixels having a value between a value corresponding to the myocardial portion, and a value corresponding to the myocardium, which are contrasted by the contrast medium.

Then, operation of the X-ray CT apparatus 1 will be described.

Figure 5:
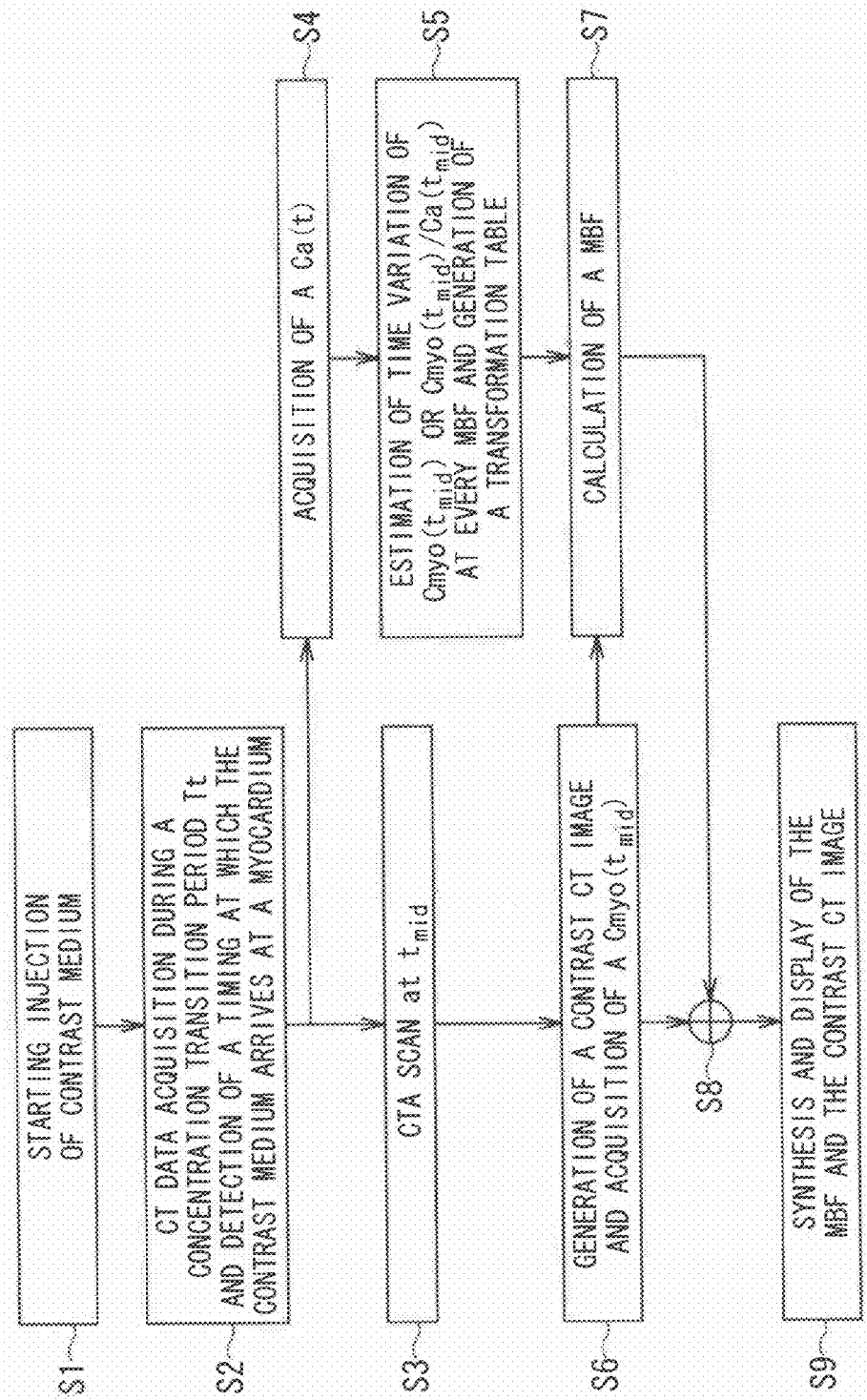
FIG. 5 is a flowchart illustrating a procedures example for generating a myocardial perfusion image by the X-ray CT apparatus illustrated in FIG. 1.

FIG. 5 is a flowchart illustrating a procedures example for generating a myocardial perfusion image by the X-ray CT apparatus 1 illustrated in FIG. 1, wherein each reference character made up of a character S and a number represents a step in the flowchart.

First, in Step S1, the contrast-medium injector 8 is controlled by a control signal from the scanning control device 18, a contrast medium is continuously injected into the object P in accordance with a certain condition from the contrast-medium injector 8, as illustrated in FIG. 4.

Then, in Step S2, myocardial CT data in the coronary artery or the left ventricular lumen is acquired during the concentration transition period Tt of the contrast medium under control by the scanning control device 18. Since the CT data acquired during the concentration transition period Tt does not used for generating an image to be displayed, it is desired to perform data acquisition with a dose less than that for after-mentioned data acquisition during the constant concentration period T1 in view of reducing dosage. Further, a timing at which the contrast medium passes through the parts including myocardial left ventricular lumen and reaches the myocardium is detected based on the acquired CT data. That is, contrast CT image data at an arbitrary slice position on the specific myocardial part is dynamically acquired synchronously with an electrocardiogram during the concentration transition period Tt in which the contrast medium concentration Cmyo(t) within the myocardial region is sufficiently smaller than the contrast medium concentration Ca(t) in the coronary artery or the left ventricular lumen.

More specifically, the electrocardiograph 9 detects an ECG signal via the unshown electrodes bonded to the object P. The electrocardiograph 9 acquires an electrocardiogram and provides this to the scanning control device 18. The scanning control device 18 provides a control signal to the high-voltage generator 5 based on the electrocardiogram acquired by the electrocardiograph 9. Consequently, the high-voltage generator 5 supplies a tube current and tube voltage to the X-ray tube 4 synchronously with an electrocardiography wave, and X-rays are radiated upon the object P.

The X-ray detector 6 detects the X-rays radiated upon the object P and passed through the object P. An X-ray detection signal output from the X-ray detector 6 is provided to the DAS 7, where digitized raw data is generated. The DAS 7 provides the generated raw data to the preprocessing unit 20, and the preprocessing unit 20 subjects the raw data to preprocessing such as various types of correction processing so as to convert the raw data into projection data. The projection data obtained by the preprocessing unit 20 is temporally stored in the memory unit 21, and then provided to the image reconstruction unit 22. The image reconstruction unit 22 reconstructs CT image data from the projection data, and the reconstructed CT image data is recorded and stored in the storage device 23.

The contrast medium is injected into the object P, so the CT image data to be stored in the storage device 23 becomes contrast CT image data. The CT image is collected synchronously with an electrocardiogram, so a myocardial contrast axial cross-sectional image can be obtained at the same period of each myocardial portion in a myocardial reduction or expansion period. The image acquisition unit 24a acquires the contrast CT image data stored in the storage device 23, and provides this to the myocardial perfusion image generating system 24.

Upon the concentration transition period Tt elapsing, the contrast medium concentration Ca(t) within the coronary artery or the left ventricular lumen of the object P becomes a state in which the concentration or the temporal change rate is considered to be constant. Moreover, the contrast medium concentration Cmyo(t) within the myocardial portion becomes a state in which the concentration or the temporal change rate is considered to be constant.

Consequently, the scanning control device 18 automatically detects the timing at which the contrast medium reaches the myocardium using the aforementioned arbitrary method. Alternatively, an arrangement may be made wherein an electrocardiogram-synchronous CT image or the variation curve of the contrast medium concentration as illustrated in FIG. 4 is graphically displayed, and the user can visually recognize the timing at which the contrast medium reaches the myocardium.

Next, in Step S3, the scanning control device 18 starts a helical angio-scan with moving the unshown table synchronously with the timing at which certain delay time is elapsed as necessary. This scan can be considered to be performed at the representative time $t_{mid}$ though it is actually performed continuously. The coronary artery contrast CT image data in the entire myocardium is acquired synchronously with an electrocardiogram after the concentration transition period Tt of the contrast medium in the myocardial portion. At this time, an axial cross-sectional image set is acquired at each slice of the same cycle in a series of cycles from reduction to expansion of the myocardium for diagnosis of the myocardium as necessary. Various types of image regarding the myocardium, such as a short-axial cross-sectional image, long-axial horizontal tomographic image, and long-axial vertical tomographic image can be obtained due to the cross-section conversion of the acquired respective axial cross-sectional images.

On the other hand, in Step S4, the blood-flow image generating unit 24e acquires the contrast CT image data, of the coronary artery or the left ventricular lumen acquired during the concentration transition period Tt, from the storage device 23 via the image acquisition unit 24a to calculate the variation curve Ca(t) of the contrast medium concentration by subtracting the CT value of only the myocardium from the acquired contrast CT image data.

Figure 6:
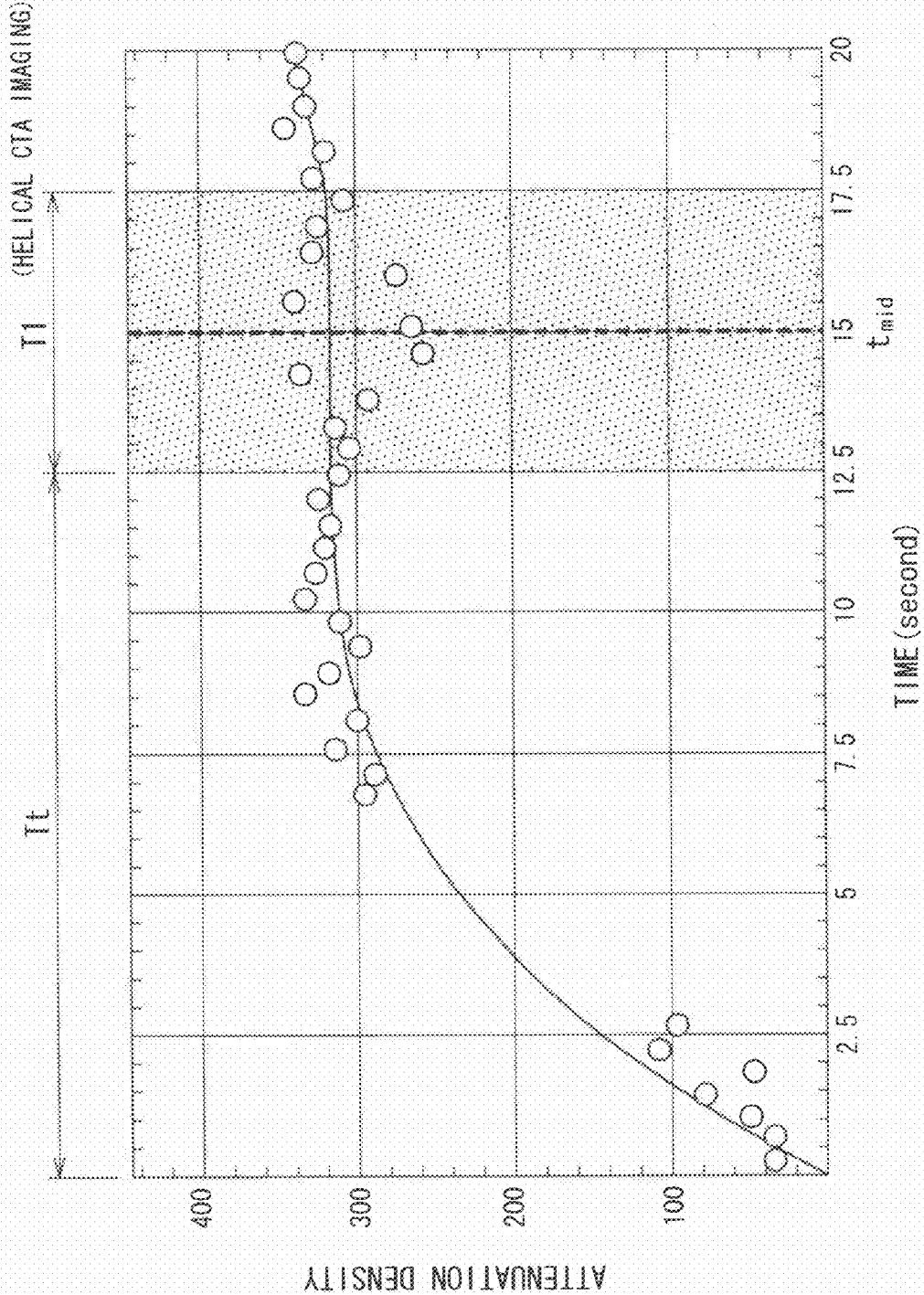
FIG. 6 is a diagram indicating CT values at the respective times calculated based on the contrast CT image data of the coronary artery or the left ventricular lumen during the concentration transition period of the contrast medium by the X-ray CT apparatus shown in FIG. 1 and a variation curve $Ca(t)$ of the contrast medium concentration obtained by a curve approximation of each CT value.

FIG. 6 is a diagram indicating CT values at the respective times calculated based on the contrast CT image data of the coronary artery or the left ventricular lumen during the concentration transition period Tt of the contrast medium by the X-ray CT apparatus 1 shown in FIG. 1 and a variation curve Ca(t) of the contrast medium concentration obtained by a curve approximation of each CT value.

A variation curve Ca(t) of the contrast medium can be calculated by curve-approximating a temporal variation of the contrast medium concentration during the concentration transition period Tt shown by dots in FIG. 6.

Subsequently in step S5, the blood-flow image generating unit 24e calculates a estimated curve indicating the contrast medium concentration Cmyo(t) in the myocardial region at a specific time t and at a specific myocardial blood flow (MBF) based on a previously acquired Vd value with setting the variation curve Ca(t) of the contrast medium concentration in the coronary artery or the left ventricular lumen as an input function. The contrast medium concentration Cmyo(t) in the myocardial region is equivalent to an increasing amount of CT value due to the contrast medium in the myocardial region.

Figure 7:
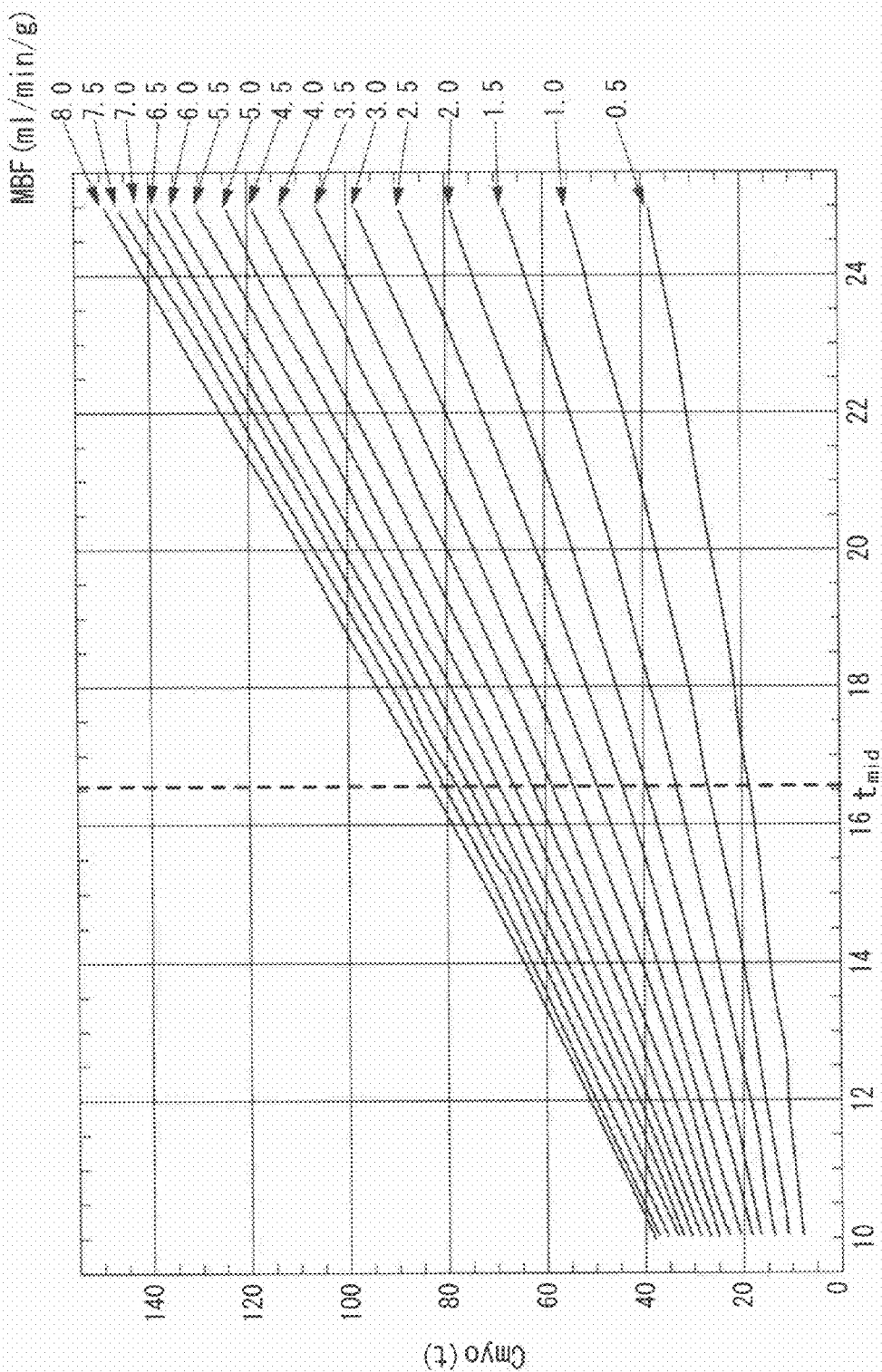
FIG. 7 is a diagram showing an estimated curve indicating the contrast medium concentration $Cmyo(t)$ in the myocardial region at every myocardial blood flow (MBF) obtained based on the variation curve $Ca(t)$ of the contrast medium concentration in the coronary artery or the left ventricular lumen shown in FIG. 6.

FIG. 7 is a diagram showing an estimated curve indicating the contrast medium concentration Cmyo(t) in the myocardial region at every myocardial blood flow (MBF) obtained based on the variation curve Ca(t) of the contrast medium concentration in the coronary artery or the left ventricular lumen shown in FIG. 6.

An estimated curve indicating the contrast medium concentration Cmyo(t) in the myocardial region at every myocardial blood flow (MBF) as shown in FIG. 7 can be obtained based on the variation curve Ca(t) of the contrast medium concentration in the coronary artery or the left ventricular lumen by the Expressions (2-2).

Further, a myocardial blood flow (MBF) and a temporal variation curve of the ratio Cmyo(t)/Ca(t) of the contrast medium concentration Cmyo(t) in the myocardial region to the variation curve Ca(t) of the contrast medium concentration in the coronary artery or the left ventricular lumen can be obtained at every myocardial blood flow (MBF), as needed.

Figure 8:
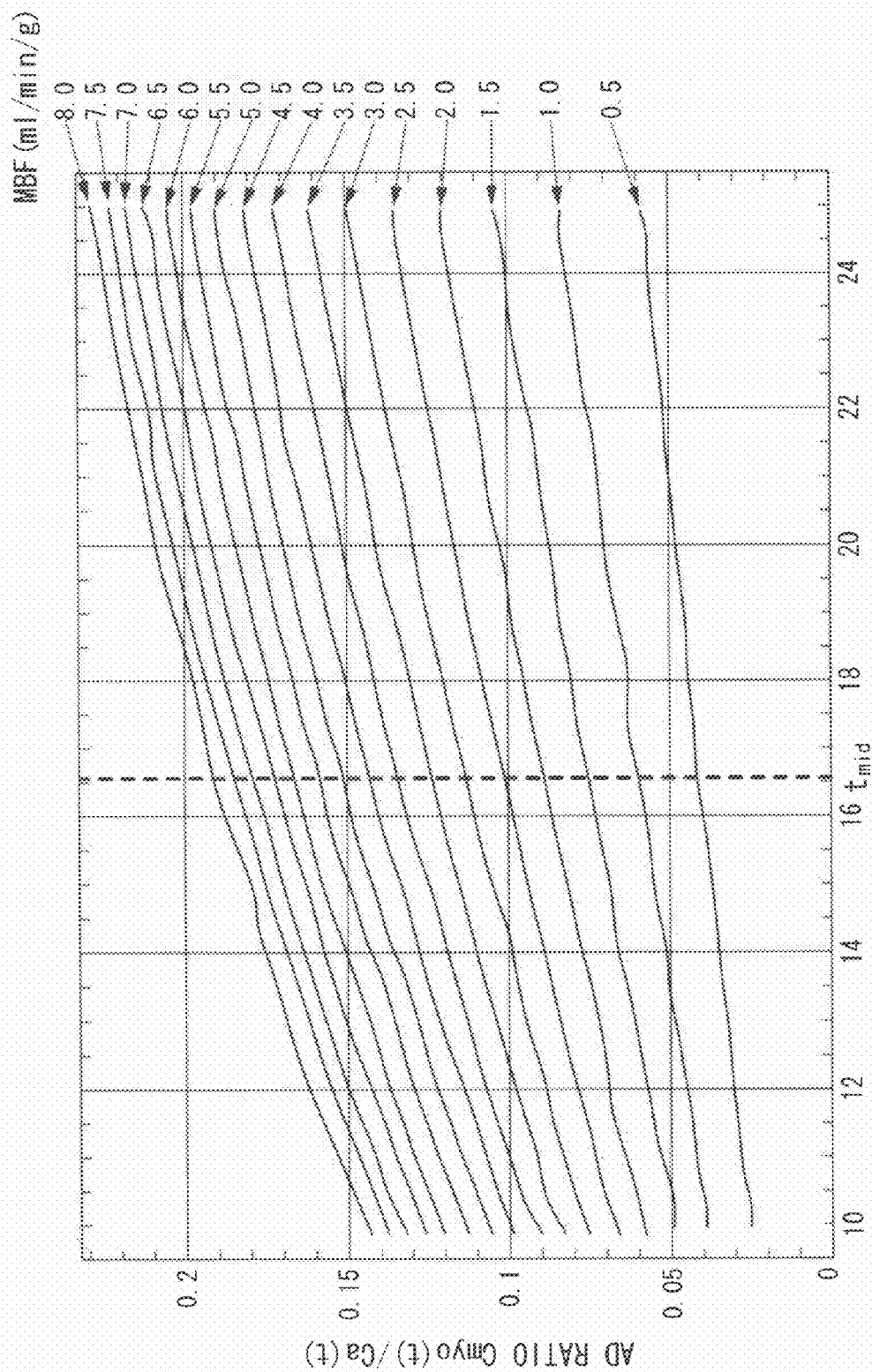
FIG. 8 is a diagram showing an estimated curve derived by dividing the contrast medium concentration $Cmyo(t)$ in the myocardial region shown in FIG. 7 by the contrast medium concentration $Ca(t)$ in the left ventricular lumen.

FIG. 8 is a diagram showing an estimated curve derived by dividing the contrast medium concentration Cmyo(t) in the myocardial region shown in FIG. 7 by the contrast medium concentration Ca(t) in the left ventricular lumen.

As shown in FIG. 8, an estimated curve of value Cmyo(t)/Ca(t) (ATtenuation density ratio AD ratio) derived by dividing the contrast medium concentration Cmyo(t) in the myocardial region shown by the contrast medium concentration Ca(t) in the left ventricular lumen can be calculated at every myocardial blood flow (MBF).

Subsequently, the blood-flow image generating unit 24e calculates a transformation table between the myocardial blood flow (MBF) corresponding to scan time $t_{mid}$ of a contrast examination and the contrast medium concentration Cmyo(t) in the myocardial region or a transformation table between the myocardial blood flow (MBF) and the concentration ratio Cmyo(t)/Ca(t) based on the temporal variation curve as shown in FIG. 7 or 8. Note that, data corresponding to a part having no data can be calculated by interpolation.

Figure 9:
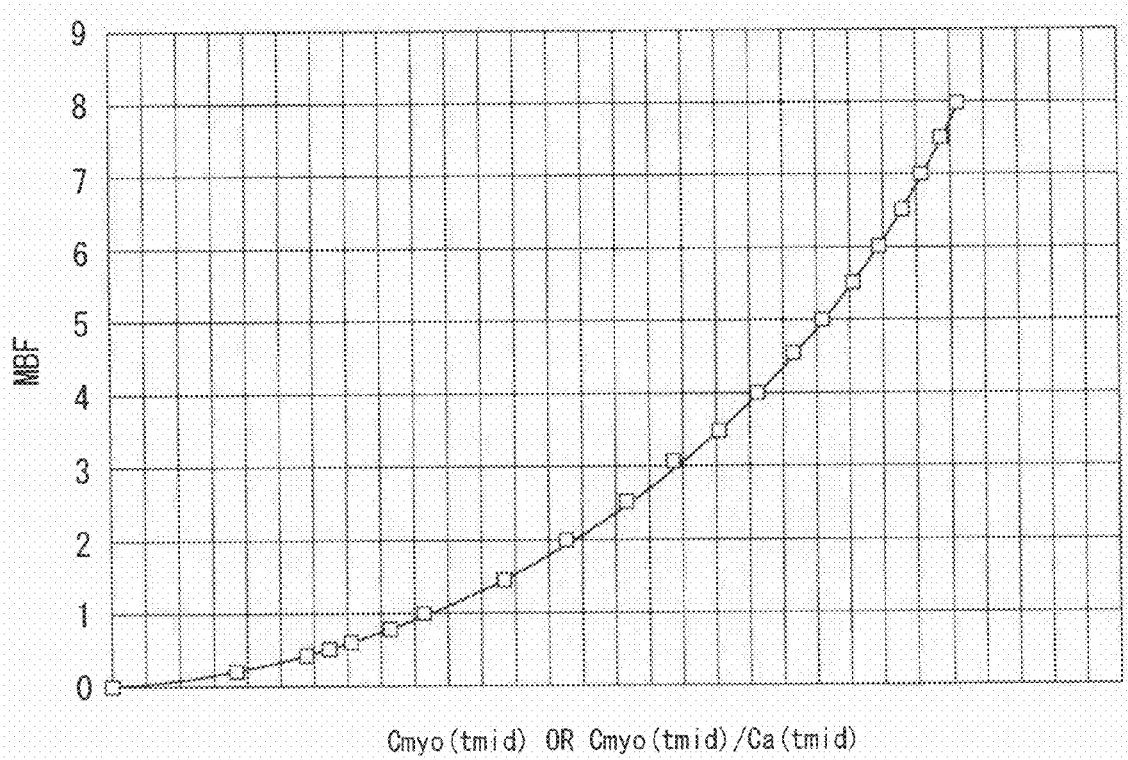
FIG. 9 is a diagram showing an example of transformation table to the myocardial blood flow (MBF) generated by the blood-flow image generating unit shown in FIG. 1.

FIG. 9 is a diagram showing an example of transformation table to the myocardial blood flow (MBF) generated by the blood-flow image generating unit 24e shown in FIG. 1.

In FIG. 9, the abscissa denotes the contrast medium concentration Cmyo(t) in the myocardial region or the value Cmyo(t)/Ca(t) derived by dividing the contrast medium concentration Cmyo(t) by the contrast medium concentration Ca(t) in the left ventricular lumen at the scan time $t_{mid}$, and the ordinate denotes the myocardial blood flow (MBF).

On the other hand, in step S6, the contrast CT image data of the entire myocardium during the constant concentration period T1 is generated through a flow equivalent to that in case of generating contrast CT image data during the concentration transition period Tt. Further, the blood-flow image generating unit 24e obtains the contrast medium concentration Cmyo($t_{mid}$) in the myocardial region at the scan time $t_{mid}$. The contrast medium concentration Cmyo($t_{mid}$) in the myocardial region can be calculated by subtracting the CT value of the myocardial region (before contrast enhancement) from the contrast CT image data (the CT value of the myocardial region after contrast enhancement).

Subsequently, in step S7, the blood-flow image generating unit 24e calculates the myocardial blood flow (MBF) based on the transformation table from the contrast medium concentration Cmyo($t_{mid}$) in the myocardial region or the concentration ratio Cmyo($t_{mid}$)/Ca($t_{mid}$) into the myocardial blood flow (MBF). Note that, calculation of the myocardial blood flow (MBF) is sufficient to be performed with regard to only a region having blood flow, within the myocardial region. However, calculation of the myocardial blood flow (MBF) may be performed with regard to the entire myocardial region according to clinical request. Here, a case of calculating the myocardial blood flow (MBF) with regard to only a region having blood flow within the myocardial region to generate a blood flow value image will be described.

Further, attempting to generate a blood flow value image of the myocardium without changing the resolution of the myocardial contrast CT image data may allow influence of noise. Consequently, the myocardial contrast CT image data is subjected to resolution reduction processing as preprocessing of generating the blood flow value image of the myocardium as necessary.

More specifically, the slice-thickness adder unit 24b receives myocardial contrast CT image data from the image acquisition unit 24a, and adds or averages the contrast CT values in the adjacent multiple slices, thereby performing the resolution reduction processing of the contrast CT image data in the slice direction. For example, the slice thickness of the myocardial contrast CT image is normally 0.5 mm or so, so in order to employ the myocardial contrast CT image data for generating a myocardial perfusion image, the resolution in the slice direction is reduced wherein the slick thickness becomes 3 mm, 5 mm, or 10 mm or so.

Furthermore, the matrix reduction unit 24c adds the contrast CT values of the myocardial contrast CT image data in each slice, or averages thereof, thereby performing matrix reduction processing.

Note that, the processing order of slice-thickness addition processing and matrix reduction processing may be in reverse order, it is arbitrary.

Next, when the resolution reduction processing is complete, the mask processing unit 24d subjects the myocardial contrast CT image data to masking, thereby extracting regions including the blood flow, of the myocardial contrast CT image data.

Then, the blood-flow image generating unit 24e calculates the myocardial blood flow (MBF) with regard to only the region having the blood flow as blood flow value image data based on the transformation table from the contrast medium concentration $Cmyo(t_{mid})$ in the myocardial region or the concentration ratio $Cmyo(t_{mid})/Ca(t_{mid})$ into the myocardial blood flow (MBF)

Figure 10:
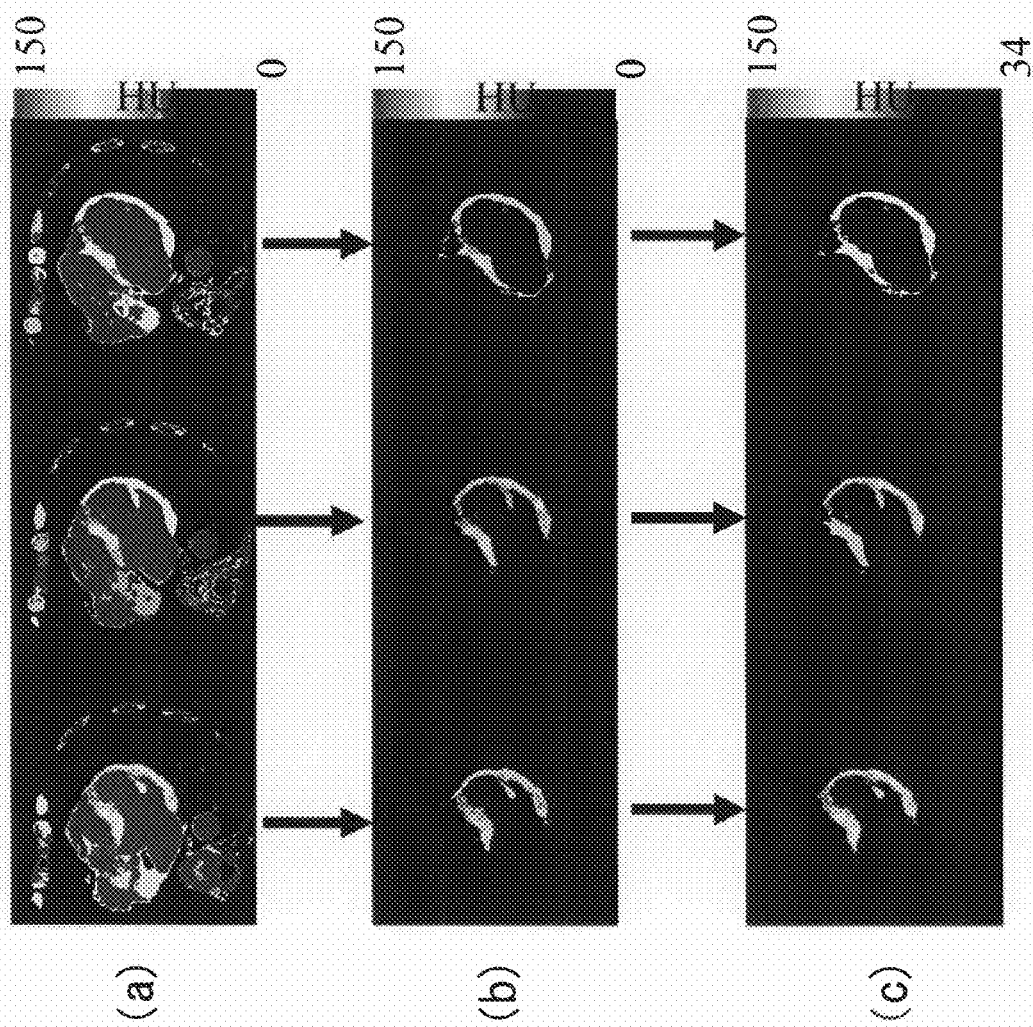
FIG. 10 is a diagram illustrating procedures for generating blood flow value image data from myocardial contrast CT image data using the X-ray CT apparatus illustrated in FIG. 1, and the obtained blood flow value image.

FIG. 10 is a diagram illustrating procedures for generating blood flow value image data from myocardial contrast CT image data using the X-ray CT apparatus 1 illustrated in FIG. 1, and the obtained blood flow value image.

In FIG. 10, (a) is the myocardial contrast CT image data in each slice following the processing of resolution reduction. The mask processing unit 24d subjects the myocardial contrast CT image data such as shown in (a) to masking, the regions including the blood flow such as shown in (b) are extracted. Here, (b) is an example subjected to masking so that the CT values become between 0 and 150 centered on the left ventricle myocardium. The extracted regions including the blood flow can be recognized from (b).

Further, the myocardial blood flow (MBF) is calculated as blood flow value image data based on the transformation table from the contrast medium concentration $Cmyo(t)$ in the myocardial region or the concentration ratio $Cmyo(t_{mid})/Ca(t_{mid})$ into the myocardial blood flow (MBF) with regard to the region having the blood flow extracted as shown in FIG. 10(b). FIG. 10(c) shows myocardial blood flow (MBF) calculated as blood flow value image data by the blood-flow image generating unit 24e.

Note that, the blood flow value image and the contrast CT value in the myocardial region are essentially the same from the perspective of display, and the difference between both is only in that the pixel values assigned to the blood flow value image are correlated with the values of the myocardial blood flow (MBF).

Furthermore, convenience at the time of diagnosis can be improved by synthesizing the blood flow value image with the contrast myocardial image for display. In this case, as for the contrast myocardial image to be synthesized with the blood flow value image, employing the high-resolution myocardial image prior to the matrix reduction processing and the addition of the contrast CT values between slices is more effective.

Consequently, in Step S8, the image synthesizing unit 24g receives the high-resolution contrast myocardial image prior to the matrix reduction processing and the addition of the contrast CT values between slices from the image acquisition unit 24a, and generates an image synthesized with the blood flow value image.

Further, the oblique cross-section converting unit 24f converts the cross section of the myocardial blood flow value image generated by the blood-flow image generating unit 24e and/or the synthesized image generated by the image synthesizing unit 24g to generate an oblique cross-section image on an arbitrary cross section, as needed.

Subsequently, in step S9, the respective images such as the blood flow value image generated by the blood-flow image generating unit 24e, the oblique cross-sectional image generated by the oblique cross-section converting unit 24f, and the synthesized image generated by the image synthesizing unit 24g are provided to the display processing unit 24h. Subsequently, the display processing unit 24h provides image signals for displaying each image to the image display unit 16 so as to display the image signals.

Now, the user can instruct automatic setting of display conditions for displaying each image through the input unit 17. The display processing unit 24h provides image signals for displaying an electronic button to the image display unit 16, for example.

Figure 11:
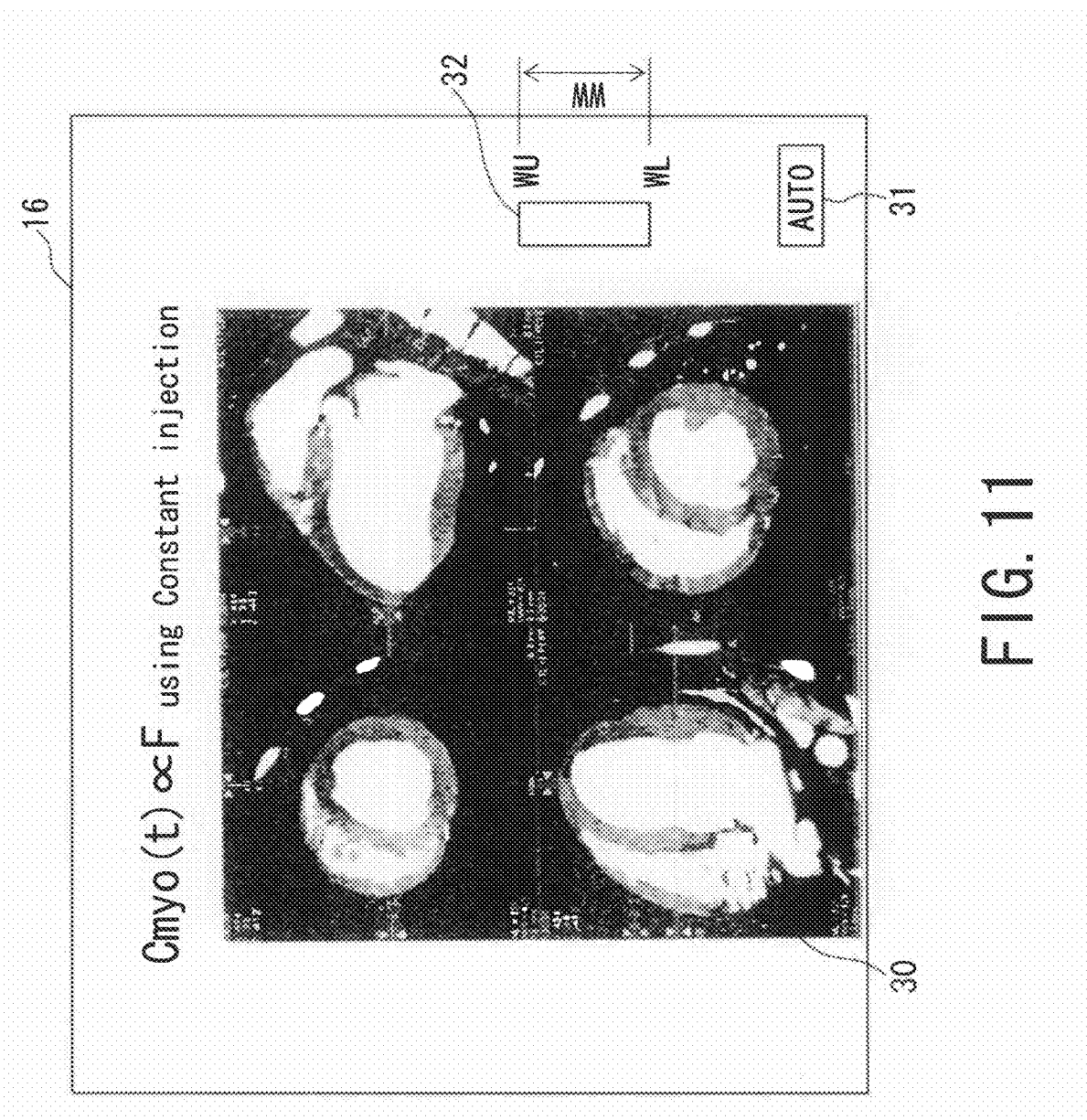
FIG. 11 is a diagram showing an example of mutually superposed blood flow value image and contrast CT image displayed and on the image display unit of the X-ray CT apparatus illustrated in FIG. 1.

FIG. 11 is a diagram showing an example of mutually superposed blood flow value image and contrast CT image displayed and on the image display unit of the X-ray CT apparatus illustrated in FIG. 1.

As illustrated in FIG. 11, a contrast CT image 30, an automatic (AUTO) button 31 for instructing automatic setting of display conditions, and a luminance scale 32 are displayed on the screen of the image display unit 16. That is to say, FIG. 11 illustrates an example in the case of displaying the blood flow value image by luminance so as to recognize the image through the grayscale.

Upon the user pressing the automatic (AUTO) button 31 by operating the input unit 17, the input unit 17 provides the automatic setting instructions of display conditions to the display processing unit 24h. In response to the instructions, the display processing unit 24h sets an appropriate value to an upper limit value WU and lower limit value WL of the luminance scale (window level), and the a width of window level WW between upper limit value and lower limit value to display a blood flow value image automatically.

More specifically, let us say that the myocardial CT value (34 or so) is A, the concentration of the contrast medium $Cmyo(t)$ within the myocardial portion is B, and an arbitrary value for fine adjustment is $\beta$, settings such as WU=A+B and WL=A+$\beta$ (accordingly, WW=B-$\beta$), or WL=A+$\beta$ and WW=A+$\beta$+$\beta$ can be performed. Consequently, the luminance scale is set to a value appropriate for displaying the blood flow value image of the myocardial portion, and the myocardial blood flow value image is displayed in grayscale by luminance as illustrated in FIG. 11.

Note that, an arrangement may be made wherein the values for determining display conditions, such as A, B, and $\beta$, can be adjusted finely by operating the input unit 17. The value of A is not restricted to the CT value, and rather may be changed according to clinical purposes. The value B may be determined experientially as a default value.

In addition to this, displaying the range between WU and WL in color may allow the user to visually recognize the blood flow value image of the myocardial portion. In the event of performing color display, gradation of color display may be divided into 16 stages visually, or may be divided into 16 stages or more, or 16 stages or less, according to stages to be recognized, for example.

The automatic (AUTO) button 31 may be displayed in the event of activating a specific application for performing myocardial blood flow display or myocardial blood flow analysis, and the like by utilizing an application program for executing image display processing, for example. Alternatively, a hardware key made up of specific hardware may be provided on the input unit 17 as the automatic (AUTO) button 31.

The X-ray CT apparatus 1 and the myocardial perfusion image generating system 24 as described above are apparatuses to calculate a transformation table between the myocardial blood flow (MBF) and the contrast medium concentration Cmyo(t) in the myocardial region or a transformation table between the myocardial blood flow (MBF) and the ratio Cmyo(t)/Ca(t) of the contrast medium concentration Cmyo(t) in the myocardial region to the variation curve Ca(t) of the contrast medium concentration in the coronary artery or the left ventricular lumen based on the variation curve Ca(t) of the contrast medium concentration in the coronary artery or the left ventricular lumen during the concentration transition period Tt of the contrast medium by injecting the contrast medium under a specific condition, and to calculate the myocardial blood flow (MBF) as a blood flow value image based on the contrast medium concentration Cmyo(t) in the myocardial region during the constant concentration period T1 according to the transformation table.

Accordingly, the X-ray CT apparatus 1 and the myocardial perfusion image generating system 24 generate a blood flow value image as a myocardial perfusion image in shorter a period with higher accuracy while further reducing the contrast medium injection rate as to the subject and dosage due to X-rays. That is, as long as the variation curve Ca(t) of the contrast medium concentration in the coronary artery or the left ventricular lumen during the concentration transition period Tt is acquired, a blood flow value image can be generated by transforming the contrast CT values in the myocardial region into the blood flow values. In addition, a blood flow value image can be generated by a single scan for contrast examination. Consequently, imaging with high speed and reducing dosage and an amount of the contrast medium to be injected can be achieved.

Note that with the aforementioned embodiment, a blood flow value image has been generated by subtracting the CT value of the myocardium alone from the myocardial contrast CT image data, but a blood flow image may be generated by subtracting a value obtained by adding/subtracting/multiplying/dividing a certain value as to the CT value of the myocardium, i.e., a certain value obtained from the CT value of the myocardium from the myocardial contrast CT image data. Further, values derived by dividing a result of subtracting the CT value of only the myocardium from contrast myocardial CT image data by a result of subtracting CT values before contrast medium administration from CT values in the left ventricular lumen at certain timing after contrast medium administration can be generated as a blood image.

What is claimed is:

1. An X-ray CT apparatus for exposing X-rays to an object so as to scan the object and reconstructing a CT image in the object based on obtained projection data, comprising:
    a transformation table acquiring unit configured to obtain a transformation table for transforming information representing a concentration of a contrast medium in a myocardium into a blood flow value image of the myocardium based on a CT image acquired in a concentration transition period defined to be a period from immediately after starting of a continuous injection of the contrast medium into the object until the contrast medium injected reaches the myocardium, increases in concentration, and is in a state in which the contrast medium is saturated at a constant value;
    a blood-flow information acquisition unit configured to obtain information representing the concentration of the contrast medium in the myocardium of the object based on a CT image acquired during a constant concentration period during which the concentration of the contrast medium in the myocardium can be considered to be constant; and
    a blood-flow image generating unit configured to generate a blood flow value image based on the information representing the concentration of the contrast medium in the myocardium according to the transformation table.

2. An X-ray CT apparatus, comprising:
    a contrast-medium injector configured to inject a contrast medium into an object so as to cause a concentration transition period defined to be a period from immediately after starting of a continuous injection of the contrast medium into the object until the injected contrast medium reaches a myocardium, increases in concentration, and is in a state in which the contrast medium is saturated at a constant value, and a constant concentration period in which a concentration of the contrast medium in the myocardium can be considered to be constant following the concentration transition period;
    an image acquiring unit configured to acquire a CT image during the concentration transition period and a CT image during the constant concentration period, each synchronized with an electrocardiogram;
    a transformation table acquiring unit configured to obtain a transformation table for transforming unspecified information representing the concentration of the contrast medium in the myocardium into a blood flow value image of the myocardium based on the CT image acquired in the concentration transition period;
    a blood-flow information acquisition unit configured to obtain information representing the concentration of the contrast medium in the myocardium of the object based on the CT image acquired during the constant concentration period; and
    a blood-flow image generating unit configured to generate a blood flow value image based on the information representing the concentration of the contrast medium in the myocardium according to the transformation table.

3. An X-ray CT apparatus according to claim 1, wherein said blood-flow information acquisition unit is configured to obtain the information representing the concentration of the contrast medium in the myocardium by performing subtraction processing between the CT image acquired during the constant concentration period and a value based on a CT value of the myocardium.

4. An X-ray CT apparatus according to claim 1, wherein said transformation table acquiring unit is configured to obtain a temporal variation of the concentration of the contrast medium in the myocardium for every blood flow in the myocardium based on a CT image acquired during the concentration transition period to obtain a transformation table corresponding to timing for acquiring the CT image acquired during the constant concentration period based on the temporal variation.

5. An X-ray CT apparatus according to claim 1, wherein said transformation table acquiring unit is configured to obtain the transformation table based on a CT image of a left ventricular lumen or a coronary artery.

6. An X-ray CT apparatus according to claim 1, wherein said blood-flow image generating unit is configured to obtain a value representing a blood flow in the myocardium as the blood flow value image.

7. An X-ray CT apparatus according to claim 1, further comprising:
a display unit configured to display the blood flow value image.

8. A myocardial perfusion image generating system comprising:
a transformation table acquiring unit configured to obtain a transformation table for transforming information representing a concentration of a contrast medium in a myocardium into a blood flow value image of the myocardium based on a CT image acquired in a concentration transition period defined to be a period from immediately after starting of a continuous injection of the contrast medium into the object until the contrast medium injected reaches the myocardium, increases in concentration, and is in a state in which the contrast medium is saturated at a constant value;
a blood-flow information acquisition unit configured to obtain information representing the concentration of the contrast medium in the myocardium of the object based on a CT image acquired during a constant concentration period during which the concentration of the contrast medium in the myocardium can be considered to be constant; and
a blood-flow image generating unit configured to generate a blood flow value image based on the information representing the concentration of the contrast medium in the myocardium according to the transformation table.

* * * * *